United States Patent [19]

Tarcsay et al.

[11] 4,414,204
[45] Nov. 8, 1983

[54] ANTIBIOTIC PREPARATIONS HAVING INCREASED EFFECTIVENESS, PROCESSES FOR THEIR MANUFACTURE AND METHOD FOR INCREASING THE ANTIBIOTIC ACTION OF ANTIBIOTICS

[75] Inventors: Lajos Tarcsay, Grenzach-Wyhlen, Fed. Rep. of Germany; Gerhard Baschang, Bettingen, Switzerland; Albert Hartmann, Grenzach, Fed. Rep. of Germany; Jaroslav Stanek, Birsfelden, Switzerland

[73] Assignee: Ciba-Geigy Corporation, Ardsley, N.Y.

[21] Appl. No.: 226,966

[22] Filed: Jan. 21, 1981

Related U.S. Application Data

[63] Continuation-in-part of Ser. No. 172,035, Jul. 24, 1980, abandoned.

[30] Foreign Application Priority Data

Jul. 25, 1979 [CH] Switzerland .................. 6893/79

[51] Int. Cl.³ ............... A61K 37/02; A61K 31/71; C07C 103/52
[52] U.S. Cl. .................... 424/177; 260/112.5 R; 424/114; 424/181; 424/180; 424/85
[58] Field of Search ............. 424/181, 177, 114, 180; 260/112.5 R

[56] References Cited

U.S. PATENT DOCUMENTS

| | | | |
|---|---|---|---|
| 3,956,481 | 5/1976 | Jolles et al. | 424/92 |
| 4,001,395 | 1/1977 | Jolles et al. | 424/92 |
| 4,082,735 | 4/1978 | Jones et al. | 260/112.5 R |
| 4,082,736 | 4/1978 | Jones et al. | 260/112.5 R |
| 4,188,384 | 2/1980 | Yoshikumi et al. | 424/180 |
| 4,268,505 | 5/1981 | Yoshikumi et al. | 424/180 |
| 4,323,560 | 4/1982 | Baschang et al. | 260/112.5 R |

FOREIGN PATENT DOCUMENTS 1570625 2/1980 United Kingdom .

OTHER PUBLICATIONS

Pp. 599–600, Hoppe-Seyler's Z. Phsiol. Chem., 358, 599, (1977).

*Primary Examiner*—Blondel Hazel
*Attorney, Agent, or Firm*—Irving N. Feit

[57] ABSTRACT

The invention relates to pharmaceutical preparations that contain an antibiotic and a muramylpeptide of the formula I or a salt thereof, to processes for their manufacture and to a method for increasing the antibiotic effectiveness of antibiotics.

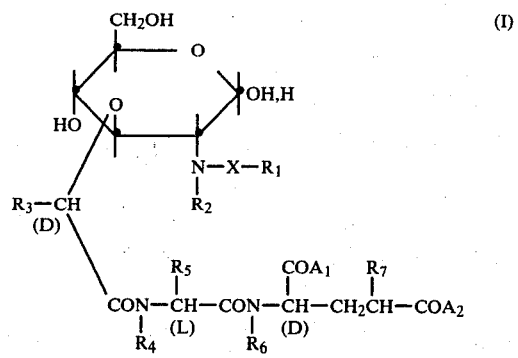

In the formula I, X represents carbonyl or carbonyloxy, $R_1$ represents optionally substituted alkyl or aryl, $R_2$, $R_3$, $R_4$ and $R_6$ represent hydrogen or lower alkyl, $R_5$ represents hydrogen, optionally substituted lower alkyl, cycloalkyl, aryl or nitrogen-containing heterocyclyl, or $R_4$ and $R_5$ together represent also $C_3$–$C_4$ alkylene, $R_7$ represents hydrogen or free, esterified or amidated carboxyl, one of the radicals $A_1$ and $A_2$ represents a radical of the formula II and the other of the radicals $A_1$ and $A_2$ represents optionally substituted or functionally modified hydroxy or amino.

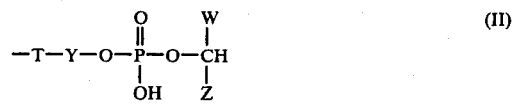

In the formula II, T represents NH or O, Y represents an optionally substituted alkylene group that can also be interrupted by oxycarbonyl or iminocarbonyl, W represents hydrogen and Z represents an optionally esterified or etherified 1,2-dihydroxyethyl or 2-hydroxyethyl group, or W and Z represent an optionally esterified or etherified hydroxymethyl group.

29 Claims, No Drawings

ANTIBIOTIC PREPARATIONS HAVING INCREASED EFFECTIVENESS, PROCESSES FOR THEIR MANUFACTURE AND METHOD FOR INCREASING THE ANTIBIOTIC ACTION OF ANTIBIOTICS

This is a continuation-in-part-application of U.S. application Ser. No. 172,035, filed July 24, 1980 now abandoned.

The present invention relates to antibiotic preparations having increased effectiveness, to processes for their manufacture and to a method for increasing the antibiotic effectiveness of antibiotics.

The invention relates especially to antibiotic preparations that contain at least one antibiotic and at least one muramylpeptide of the formula (I) or a salt thereof

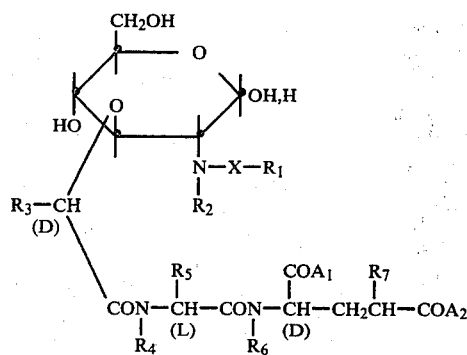

wherein

X represents carbonyl or carbonyloxy, $R_1$ represents optionally substituted alkyl or aryl, $R_2$, $R_4$ and $R_6$ represent hydrogen or lower alkyl, $R_3$ represents hydrogen or lower alkyl, $R_5$ represents hydrogen, lower alkyl, free or functionally modified hydroxy-lower alkyl, free or functionally modified mercapto-lower alkyl, optionally substituted amino-lower alkyl, cycloalkyl, cycloalkyl-lower alkyl, optionally substituted aryl or aralkyl, nitrogen-containing heterocyclyl or heterocyclyl-lower alkyl, or $R_4$ and $R_5$ together represent also alkylene having 3 or 4 carbon atoms, $R_7$ represents hydrogen or optionally esterified or amidated carboxyl, and one of the radicals $A_1$ and $A_2$ represents a radical of the formula

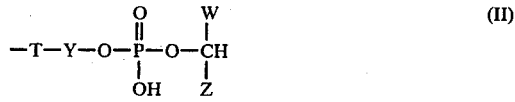

wherein

T represents NH or 0,

Y represents an optionally substituted alkylene group that can also be interrupted by one or two oxycarbonyl and/or iminocarbonyl groups, W represents hydrogen, and Z represents a 1,2-dihydroxyethyl or 2-hydroxyethyl group in which at least one hydroxy group is esterified by an optionally unsaturated long-chain aliphatic carboxylic acid or etherified by an optionally unsaturated long-chain aliphatic alcohol, or each of W and Z represents a hydroxymethyl group esterified by an optionally unsaturated long-chain aliphatic carboxylic acid or etherified by an optionally unsaturated long-chain aliphatic alcohol, and the other of the radicals $A_1$ and $A_2$ represents free or etherified hydroxy, free or alkylated amino, lower alkylamino or aminocarbonyl-lower alkylamino, and to salts thereof.

Alkyl is especially straight-chain or branched alkyl bonded in any position and having up to 18 carbon atoms, but is especially lower alkyl.

Suitable substituents of optionally substituted alkyl groups are especially free or functionally modified hydroxy or mercapto groups, such as etherified or esterified hydroxy or mercapto groups, for example lower alkoxy or lower alkylmercapto groups, or halogen atoms, or free or functionally modified carboxyl groups, such as lower alkoxycarbonyl groups or carbamoyl groups. The substituted alkyl radical, such as a lower alkyl radical, can carry one, two or more identical or different substituents, especially free hydroxy groups or halogen atoms.

Aryl radicals are especially monocyclic and bicyclic aryl radicals, especially phenyl but also naphthyl. They can optionally be mono-, di- or poly-substituted, for example by lower alkyl groups, by free, esterified or etherified hydroxy, for example lower alkoxy or lower alkylenedioxy, or by halogen atoms, and/or by trifluoromethyl groups.

Aralkyl is especially aryl-lower alkyl, wherein aryl has the meaning given above. Aryl-lower alkyl represents especially benzyl or phenylethyl, wherein the phenyl nucleus can be mono-, di- or poly-substituted.

Optionally substituted aralkyl radicals are especially those radicals that are optionally mono-, di- or poly-substituted in the aromatic nucleus, for example by lower alkyl, by free, etherified or esterified hydroxy or mercapto groups, for example lower alkoxy, lower alkylenedioxy and lower alkylmercapto groups, or by trifluoromethyl groups, and/or by halogen atoms.

Cycloalkyl is especially cycloalkyl having 5 or 6 carbon atoms, such as cyclopentyl or cyclohexyl, and cycloalkyl-lower alkyl is especially a radical in which the cycloalkyl moiety has 5 or 6 carbon atoms and the lower alkyl moiety represents especially methyl or ethyl.

Nitrogen-containing heterocyclyl is especially the radical of a 5- or 6-membered heterocyclic compound containing one or two nitrogen atoms in the ring. The radical can be unsaturated or alternatively saturated and can contain, for example, a condensed-on phenyl radical. Such radicals may be, for example, pyrrolyl, indolyl, pyridyl or imidazolyl radicals.

In nitrogen-containing heterocyclyl-lower alkyl the heterocyclyl radical has the meaning given above and the lower alkyl radical is especially methyl or ethyl.

The alkylene radical, which can be formed by the radicals $R_4$ and $R_5$, is preferably unsubstituted and is especially the trimethylene radical.

An optionally esterified or amidated carboxyl group is especially the carboxyl group itself or a carboxyl group esterified by a lower alkanol, or alternatively a carbamoyl group that is unsubstituted at the nitrogen atom or is mono- or disubstituted by alkyl, especially lower alkyl, by aryl, especially phenyl, or by aralkyl, such as benzyl. The carbamoyl group can, however, also carry an alkylene radical, such as the tetramethylene or pentamethylene radical.

As optionally functionally modified hydroxy or mercapto groups special mention may be made of etherified or esterified hydroxy or mercapto groups, such as lower alkoxy, lower acyloxy, for example lower alkanoyloxy, or halogen atoms, lower alkylmercapto or lower acylmercapto, for example lower alkanoylmercapto.

As functionally modified amino-lower alkyl special mention may be made of mono- or di-lower alkylamino-lower alkyl or acylated amino-lower alkyl, such as methylamino-lower alkyl, ethylamino-lower alkyl, dimethylamino-lower alkyl, diethylamino-lower alkyl and alkanoylamino-lower alkyl, for example lower alkanoylamino-lower alkyl.

Aminocarbonyl-lower alkylamino is especially 1-aminocarbonyl-lower alkylamino, for example glycylamino, alanylamino, valylamino or isoleucylamino.

The alkylene radical Y contains up to 20 carbon atoms and is especially a lower alkylene radical, preferably having 2 or 3 carbon atoms. The alkylene radical Y can, however, also be a lower alkylene radical interrupted by a radical such as oxycarbonyl or N—$R^a$-iminocarbonyl, and then represents especially a radical of one of the formulae $$-Y_1-COO-Y_2- \qquad (IIIa)$$
$$-Y_1-OOC-Y_2- \qquad (IIIb)$$

$$-Y_1-CON-Y_2- \qquad (IIIc)$$
$$\phantom{-Y_1-CO}|\phantom{N-Y_2-}$$
$$\phantom{-Y_1-C}R^a$$

or $$-Y_1-NOC-Y_2- \qquad (IIId)$$
$$\phantom{-Y_1-N}|\phantom{OC-Y_2-}$$
$$\phantom{-Y_1-}R^a$$

wherein one of the radicals $Y_1$ and $Y_2$ represents an optionally substituted lower alkylene radical and the other of the radicals $Y_1$ and $Y_2$ represents an optionally substituted lower alkylene radical that can also be interrupted by oxycarbonyl or N—$R^a$-iminocarbonyl, $Y_1$ and $Y_2$ together having more than two carbon atoms, and $R^a$ represents hydrogen or lower alkyl. As substituents of the radicals $Y_1$ and $Y_2$ special mention should be made of free or functionally modified hydroxy or hydroxy-lower alkyl, free or functionally modified mercapto or mercapto-lower alkyl, free, mono- or di-lower alkylated or acylated amino-lower alkyl, aminocarbonyl, alkyl, cycloalkyl having 5 or 6 carbon atoms, aryl or aralkyl, it being possible for the general terms to have the meanings specified above.

A long-chain aliphatic carboxylic acid is especially one that has from 10 to 90 carbon atoms and that may also have 1 or 2 double bonds and may be straight or branched. Preferred are those having up to 30 carbon atoms, especially from 16 to 22 carbon atoms, or natural or synthetic mycolic acids.

A long-chain aliphatic alcohol is especially an alkanol that has up to 30 carbon atoms, especially from 10 to 22 carbon atoms, and that may also have one or two double bonds and may be straight or branched. Preferred are those alkanols which contain from 12 to 18 carbon atoms and of which the hydroxy group is terminal.

Those radicals and compounds that are termed "lower" in connection with the present description and the patent claims preferably contain up to and including 7 carbon atoms and especially up to and including 4 carbon atoms.

Hereinbefore and hereinafter the general terms can have the following meanings:

Lower alkyl is, for example, n-propyl, n-butyl, isobutyl, sec.-butyl or tert.-butyl, also n-pentyl, n-hexyl, isohexyl or n-heptyl, and especially methyl or ethyl. In aryl-lower alkyl, cycloalkyl-lower alkyl or heterocyclyl-lower alkyl radicals the lower alkyl radical is especially methyl or ethyl, the aryl, cycloalkyl or heterocyclyl radical having the meaning given above.

Lower alkoxy is, for example, n-propoxy, n-butoxy, isobutoxy, sec.-butoxy or tert.-butoxy and especially methoxy or ethoxy.

Lower alkylmercapto is, for example, n-propylmercapto, n-butylmercapto, isobutylmercapto, sec.-butylmercapto or tert.-butylmercapto and especially methylmercapto or ethylmercapto.

Lower alkylenedioxy is especially methylenedioxy, ethylenedioxy or propylenedioxy.

Halogen represents fluorine or bromine but preferably chlorine.

Lower alkanoyl is especially propionyl or butyryl but more especially acetyl.

Synthetic mycolic acids are especially α-alkyl-β-hydroxyalkanecarboxylic acids, wherein the alkyl radical in the α-position contains from 1 to 20, especially 1 to 14, carbon atoms, and the alkanecarboxylic acid contains from 20 to 80, especially from 30 to 34, carbon atoms. They can also contain further hydroxyl groups, and oxo, methylene or ethylene groups.

Natural mycolic acids are especially those which can be isolated from living organisms, such as bacteria, for example Mycobacteria.

The compounds of the formula I can be present in the form of isomeric mixtures or in the form of pure isomers. The radical of the formula —CH($R_3$)—(C=O)—, which is linked to the oxygen atom, if $R_3$ represents lower alkyl, is preferably present in optically active form and has especially the D-form, while the radical of the amino acid of the formula —N($R_4$)—CH($R_5$)—C(=O), if $R_5$ is different from hydrogen, is also preferably present in optically active form, especially in the L-form, and the terminal α-amino-glutaric acid radical is preferably present in optically active form, especially in the D-form. Further, the 1-hydroxy group can have the α- or the β-configuration. The novel compounds of the formula I can, however, also be present in the form of a mixture of the 1α-and 1β-isomers.

In the compounds of the formula I the proton linked to phosphorus via an oxygen atom can be split off readily with bases. The compounds of the formula I are customarily present in the form of a mixture of the free compounds and their salts. Approximately 40 to 55% of the muramylpeptides of the formula I described in the Examples are thus present in the form of sodium salts. The invention relates also to these salts as combination partners.

The invention relates generally also to the salts of compounds of the formula I having any other salt-forming groups, for example free carboxyl groups, especially pharmaceutically acceptable non-toxic salts, for example metal or ammonium salts.

Compounds of the formula I having amino groups, for example in the radical $R_5$, can be present in the form of internal salts (zwitterions) or in the form of acid addition salts. Weak and pharmaceutically acceptable acids are especially suitable for addition. Any antibiotics are suitable as combination partners. It is possible to use both individual antibiotics and mixtures of antibiotics. The latter preferably contain not more than three compounds having antibiotic action. There are used especially antibiotics from the group consisting of β-lactam antiobiotics, aminoglycosides, tetracyclines, macrolides, lincomycins, polyene antibiotics, polypeptide antibiotics, anthracyclines, chloramphenicols and thiamphenicols, cycloserines, fusidic acids or rifamycins.

As preferred antibiotics from among the β-lactams there may be mentioned the penicillins, cephalosporins, penems, nocardicins, thienamycins and clavulanic compounds.

Penicillin antibiotics are especially amoxycillin, ampicillin, carbenicillin, cloxacillin, cyclacillin, dicloxacillin, mecillinam, methicillin, penicillin G, penicillin V, pivampicillin, sulbenicillin, azlocillin, ticarcillin, mezlocillin, pivmecillinam or 6-(4-endoazatricyclo[5.2.2.0$^{2,6}$]undec-8-enyl)-methyleneaminopenicillanic acid.

From the group of cephalosporins there may be mentioned, for example, cefaclor, cefazaflur, cefazolin, cefadroxil, cefoxitin, cefuroxime, cephacetril, cephalexin, cephaloglycin, cephaloridins, cephalothin, cefamandole, cephanon, cephapirin, cefatrizine, cephradine, cefroxadin (7β-[D-2-amino-2-(1,4-cyclohexadienyl)-acetamido]-3-methoxy-3-cephem-4-carboxylic acid=CGP 9000), cefsulodin, cefotaxime, cefotiam, ceftezole or cefazedon.

Of the nocardicins there may be mentioned, for example, nocardicin A, and of the thienamycins and clavulanic acids there may be mentioned, for example, thienamycin and clavulanic acid respectively.

Of the aminoglycosides special mention should be made of streptomycins, for example streptomycin and streptomycin A, neomycins, for example neomycin B, tobramycins, for example tobramycin or dibekacin, kanamycins, (for example mixtures of kanamycin A, B and C), and amicacins, gentamycins, (for example mixtures of gentamycin A, $C_1$, $C_2$ or $C_{1a}$), or sisomycins such as sisomycin or netilmycin, also lividomycin, ribocamycin and paromomycin.

As tetracyclines special mention should be made of tetracycline, doxycycline, chlorotetracycline, oxytetracycline or methacycline.

As macrolides there may be mentioned, for example, maridomycin, spiramycins, such as spiramycin I, II and III, erythromycins, for example erythromycin, oleandomycins, for example oleandomycin and tetraacetyloleandomycin, and, as lincomycins, for example, lincomycin and clindamycin.

As polyene antiobiotics special mention should be made of amphothericin B and the methyl ester thereof, or nystalin.

As polypeptide antibiotics special mention may be made, for example, of colistin, gramicidin S, polymyxin B, virginiamycin, tyrothricin, viomycin or vancomycin.

Suitable rifamycins are especially rifamycin S, rifamycin SV or rifamycin B or semisynthetic derivatives thereof, especially rifampicin.

The combination preparations according to the invention contain the customary amounts of antibiotics per dosage unit, for example between 50 and 1000 mg, as a rule between 100 and 500 mg. The amount of muramylpeptide depends upon the intended method of administration. The amount for orally administrable preparations is higher than that for injectable preparations.

Orally administrable preparations contain muramylpeptide of the formula I in an amount from 1 mg to half the amount of antibiotics, as a rule between 5 and 50 mg. When using coated tablets that are resistant to gastric juice the dose can also be less than 1 mg (down to 0.01 mg) of muramylpeptide per tablet. Injectable preparations contain between 10 μg and 50 mg, preferably between 100 μg and 10 mg, of muramylpeptide. These preparations can additionally contain the customary amounts of pharmacological carriers, extenders and/or diluents, especially when they are to be used for oral administration. Liposomal forms of administration are also suitable especially for injectable preparations.

Special emphasis is to be given to pharmaceutical or veterinary preparations, as well as animal feedstuffs or feedstuffs additives, which contain an effective or less than effective dose of the specified antibiotics and, in addition, a muramylpeptide of the formula I.

The pharmaceutical preparations of the present invention are preferably tablets or gelatin capsules which contain the active substances together with diluents, for example lactose, dextrose, saccharose, mannitol, sorbitol, cellulose and/or glucose, and lubricants, for example siliceous earth, talc, stearic acid or salts thereof, such as magnesium or calcium stearate, and/or polyethylene glycol. Tablets also contain binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example, starches, agar, alginic acid or a salt thereof, such as sodium alginate, and/or effervescent mixtures, or adsorbents, colourants, flavourings and sweeteners. Injectable preparations are preferably isotonic aqueous solutions or suspensions. Suppositories, ointments or creams are especially fatty emulsions or suspensions. The pharmaceutical preparations can be sterilised and/or contain adjuncts, for example preservatives, stabilisers, wetting agents and/or emulsifiers, solubilisers, salts or regulating the osmotic pressure and/or buffers. The present pharmaceutical preparations which, if desired, can contain further pharmacologically valuable substances, are manufactured in a manner known per se, for example by means of conventional mixing, granulating or coating methods, and contain from approximately 0.1% to approximately 75%, especially from approximately 1% to approximately 50%, of the specified active substances.

The orally administrable preparations of the present invention can also be provided with a coating that is resistant to gastric juice.

The high antibiotic action of the novel preparations and of the novel method can be demonstrated by "in vivo" tests on various species of animals, especially mammals such as mice. For this purpose, animals are infected with a lethal or sub-lethal dose of a pathogenic micro-organism and then the specified novel preparation of the individual doses of muramylpeptide and antibiotic are administered. The action is determined as $ED_{50}$, that is to say, the dose at which 50% of the animals survive.

Surprisingly, it has now been found that infection with pathogenic germs, especially of the less easily controllable gram-negative bacteria, such as, for example, strains of Aerobacter, Brucella, Escherichia, Klebsiella, Malleomyces, Neisseria, Pasteurella, Proteus, Pseudomonas, Shigella and Vibro, but also a gram-positive bacteria such as actinomycetes, clostridia, corynebacteria, diplococci, mycobacteria or staphylococci, or of fungi such as *Candida albicans, Cryptococcus neoformans, Plastomyces dermatitides* or *Hystoplasma capsulatum,* are inhibited and combated to an increased extent.

The invention relates also to a method for increasing the antibiotic activity of antibiotics. This method is characterised in that at least one antibiotic, especially an antibiotic as described in the combination preparations according to the invention, is administered together with at least one of the above-mentioned muramylpeptides of the formula I.

In the method of the present invention, an effective or less than effective dose of the antibiotic is used depending on the nature of the latter, for example from approximately 10 to approximately 1000 mg, especially from approximately 50 to approximately 500 mg, per individual dose.

The dosage of muramylpeptides of the formula I depends on the method of administration and corresponds to the dosage specified for the pharmaceutical preparations. The muramylpeptide derivative can be administered up to 24 hours before or after, but preferably approximately simultaneously with, the antibiotic.

The antibiotics are administered in the customary manner, such as subcutaneously, intravenously or orally, while the muramylpeptides are usually administered subcutaneously, especially when they are administered separately from the antibiotics.

Especially suitable as combination partners are muramylpeptides of the formula I

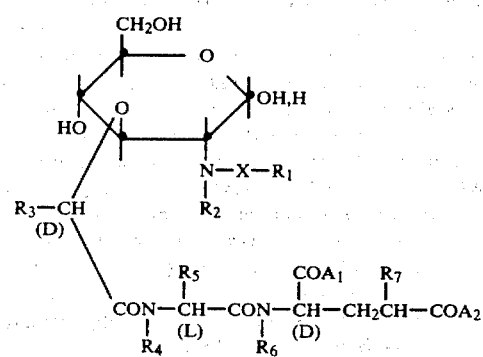

wherein

X represents carbonyl, $R_1$ represents optionally substituted alkyl having up to 18 carbon atoms or aryl having up to 30 carbon atoms, $R_2$, $R_3$, $R_4$ and $R_6$ represent hydrogen or lower alkyl, $R_5$ represents hydrogen; lower alkyl optionally substituted by hydroxy, lower alkoxy, mercapto, lower alkylmercapto, amino, lower alkylamino or by halogen; cycloalkyl or cycloalkyl-lower alkyl, wherein the cycloalkyl radical contains from 4 to 6 carbon atoms; optionally substituted phenyl or phenyl-lower alkyl; heterocyclyl or heterocyclyl-lower alkyl, each having 5 or 6 ring members and containing one or two aza atoms, or $R_4$ and $R_5$ together represent also alkylene having 3 to 4 carbon atoms, $R_7$ represents hydrogen, and one of the radicals $A_1$ and $A_2$ represents a radical of the formula

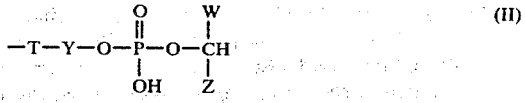

wherein

T represents NH or O,

Y represents optionally substituted alkylene that has up to 20 carbon atoms and can also be interrupted by carbonyloxy or carbonylimino, W represents hydrogen, and Z represents a 1,2-dihydroxyethyl or 2-hydroxyethyl group in which at least one hydroxy group is esterified by an optionally unsaturated long-chain aliphatic carboxylic acid having up to 30 carbon atoms or by a mycolic acid, or is etherified by an optionunsaturated longchain aliphatic alcohol having up to 30 carbon atoms, or each of W and Z represents a hydroxymethyl group esterified by an optionally unsaturated long-chain aliphatic carboxylic acid having up to 30 carbon atoms or by a mycolic acid or etherified by an optionally unsaturated long-chain aliphatic alcohol having up to 30 carbon atoms, and the other of the radicals $A_1$ and $A_2$ represents free or etherified hydroxy, amino, lower alkylamino or aminocarbonyl-lower alkylamino, and salts thereof.

Preferred combination partners are muramylpeptides of the formula I wherein X represents carbonyl, $R_1$ represents lower alkyl optionally substituted by hydroxy, lower alkoxy or by halogen; or phenyl optionally substituted by hydroxy, lower alkoxy, lower alkyl or by halogen, $R_2$, $R_4$ and $R_6$ represent hydrogen or methyl, $R_3$ represents hydrogen, methyl or ethyl, $R_5$ represents hydrogen; lower alkyl having from 1 to 7 carbon atoms optionally substituted by hydroxy, lower alkoxy, mercapto, lower alkylmercapto or by halogen; 4-aminobutyl; cycloalkyl or cycloalkyl-lower alkyl wherein the cycloalkyl radical contains from 4 to 6 carbon atoms and the lower alkyl radical contains from 1 to 3 carbon atoms; phenyl or phenyl-lower alkyl having from 1 to 3 carbon atoms in the lower alkyl radical and optionally substituted by hydroxy, lower alkoxy or by halogen; 4-imidazolylmethyl or 3-indolylmethyl, or $R_4$ and $R_5$ together represent also alkylene having 3 to 4 carbon atoms, $R_7$ represents hydrogen and one of the radicals $A_1$ and $A_2$ represents a radical of the formula

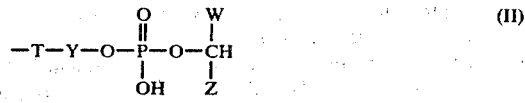

wherein T represents NH or O, Y represents optionally substituted lower alkylene or a radical of the formulae

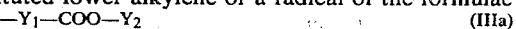

$$-Y_1-COO-Y_2 \quad \text{(IIIa)}$$

or

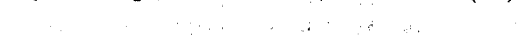

$$-Y_1-CONH-Y_2 \quad \text{(IIIe)}$$

in which each of $Y_1$ and $Y_2$ independently of the other represents lower alkylene that has from 1 to 7 carbon atoms and is optionally substituted by hydroxy, lower alkoxy, mercapto, methylthio, phenyl, 4-imidazolyl or by 3-indolyl, W represents hydrogen and Z represents a 1,2-dihydroxyethyl or 2-hydroxyethyl group in which at least one hydroxy group is esterified by an aliphatic carboxylic acid having from 14 to 24 carbon atoms and optionally containing one or two unsaturated bonds, or by a natural or synthetic mycolic acid or etherified by an aliphatic alcohol having from 10 to 20 carbon atoms and optionally containing one or two unsaturated bonds, or each of W and Z represents a hydroxymethyl group esterified by an aliphatic carboxylic acid having from 16 to 22 carbon atoms and optionally containing one or two unsaturated bonds, or by a natural or synthetic mycolic acid or etherified by an aliphatic alcohol having from 12 to 18 carbon atoms and optionally containing one or two unsaturated bonds, and the other of the radicals $A_1$ and $A_2$ is hydroxy, lower alkoxy, amino, lower alkylamino or aminocarbonyl-lower alkylamino, and salts thereof.

Especially preferred combination partners are muramylpeptides of the formula I wherein X represents carbonyl, $R_1$ represents lower alkyl or phenyl, $R_2$, $R_6$ and $R_7$ represent hydrogen, $R_3$ and $R_4$ represent hydrogen or methyl, $R_5$ represents hydrogen, lower alkyl having from 1 to 7 carbon atoms optionally substituted by phenyl, or $R_4$ and $R_5$ together represent also trimethylene, wherein $A_1$ represents hydroxy, lower alkoxy, amino, lower alkylamino or aminocarbonyl-lower alkylamino and $A_2$ represents a radical of the formula

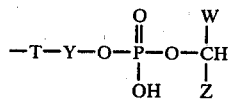

wherein T represents NH or O, Y represents ethylene or a radical of the formulae $$Y_1-COO-Y_2 \text{ or } Y_1-CONH-Y_2$$

(IIIa)  (IIIe)

wherein each of $Y_1$ and $Y_2$ indpendently of the other represents unsubstituted lower alkylene, W is hydrogen and Z is a 1,2-dihydroxyethyl or 2-hydroxyethyl group in which at least one hydroxy group is esterified by an alkanecarboxylic acid having from 16 to 20 carbon atoms and optionally containing one or two unsaturated bonds, or etherified by an alkanol having from 12 to 18 carbon atoms and optionally containing one or two unsaturated bonds, or each of W and Z represents a hydroxymethyl group esterified by an alkanecarboxylic acid having from 16 to 22 carbon atoms and optionally containing one or two unsaturated bonds, or etherified by an alkanol having from 12 to 18 carbon atoms and optionally containing one or two unsaturated bonds, and those compounds in which the meanings for $A_1$ and $A_2$ are interchanged and salts thereof.

Most especially preferred as combination partners are muramylpeptides of the formula I wherein X represents carbonyl, $R_1$ represents lower alkyl or phenyl, $R_2$, $R_4$, $R_6$ and $R_7$ represent hydrogen, $R_3$ represents hydrogen or methyl, $R_5$ represents lower alkyl having from 1 to 3 carbon atoms, $A_1$ represents amino and $A_2$ represents a radical of the formula

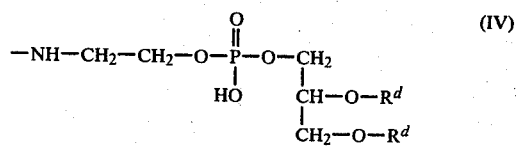

wherein $R^d$ represents the acyl radical of an alkanecarboxylic acid having from 16 to 20 carbon atoms and optionally containing one or two unsaturated bonds, and salts thereof.

The novel phosphorylmuramylpeptides of the formula I can be prepared according to various processes that are known per se. They are prepared, for example, by condensing, in a manner known per se, a compound of the formula V

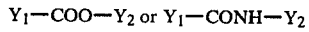

wherein X, $R_1$, $R_2$, $R_3$, $R_4$, $R_5$, $R_6$ and $R_7$ have the meanings given above $R_8$, $R_9$ and $R_{10}$ represent hydrogen or a protecting group that can readily be split off and one of the radicals $A_1{}^o$ and $A_2{}^o$ represents an activated hydroxy group and the other of these radicals is etherified hydroxy, amino, lower alkylamino or aminocarbonyl-lower alkylamino, with a compound of the formula (VI), $$\underset{\underset{OH}{|}}{H-T-Y-O-\overset{\overset{O}{\|}}{P}-O-\overset{\overset{W}{|}}{\underset{\underset{Z}{|}}{CH}}} \quad (VI)$$

wherein T, Y, W and Z have the meanings specified for the end products, and splitting off the protecting groups that are present.

The activated carboxylic acid group $COA_1{}^o$ or $COA_2{}^o$ can be, for example, an acid anhydride, for example with a carbonic acid lower alkyl ester, such as carbonic acid ethyl ester or carbonic acid isobutyl ester, an acid azide, an acid amide, such as an imidazolide, isoxazolide or an activated ester. As activated esters special mention may be made of: cyanomethyl ester, carboxymethyl ester, p-nitrophenyl ester, methoxyethylthio ester, acetylaminoethylthio ester, p-nitrophenyl ester, 2,4,5-trichlorophenyl ester, N-hydroxysuccinimide ester, N-hydroxyphthalimide ester, 8-hydroxyquinoline ester, N-hydroxypiperidine ester. Active esters can also be obtained optionally with a carbodiimide with the addition of N-hydroxysuccinimide or a 1-hydroxybenzotriazole or 3-hydroxy-4-oxo-3,4-dihydrobenzo[d]-1,2,3-triazine that is unsubstituted or substituted, for example by halogen, methyl or methoxy.

Preferred active esters are those with N-hydroxysuccinimide or the C-substitution products thereof, such as N-hydroxymethylsuccinimide or N-hydroxydimethylsuccinimide, or activation by reacting with a carbodiimide, such as carbodiimide itself or 1-ethyl-3-(3-dimethylaminopropyl)-carbodiimide is preferred.

The starting materials used for this purpose are known or may be prepared in a manner known per se.

If in the novel compounds of the formula I T represents O, this reaction may also be carried out in such a manner that the free acid is esterified with the alcohol in the presence of an agent that splits off water, such as a carbodiimide, for example dicyclohexylcarbodiimide, and an amine, such as pyridine and dimethylaminopyridine, or a trialkylamine, for example trimethylamine. It is also possible, however, to react the carboxylic acid, for example in the form of a salt, such as a sodium or potassium salt, with a reactive ester of the alcohol, for example an ester with a strong inorganic or organic acid, such as a hydrohalic acid, for example hydrochloric, hydrobromic or hydriodic acid, or an organic sulphonic acid, such as p-toluenesulphonic acid or methanesulphonic or ethanesulphonic acid. Furthermore, it is also possible to react the alcohol, optionally in the form of a salt, for example a sodium or potassium salt, with an activated carboxylic acid.

Protecting groups that can readily be split off are those known from peptide or sugar chemistry. For carboxy groups special mention should be made of tertiary-butyl, benzyl or benzhydryl, and for hydroxy groups special mention should be made of acyl radicals, for example lower alkanoyl radicals, such as acetyl, aroyl radicals, such as benzoyl, and more especially radicals that are derived from carbonic acid, such as benzyloxycarbonyl or lower alkoxycarbonyl, or alkyl, especially tert-butyl, benzyl optionally substituted by nitro, lower alkoxy or by halogen, or tetrahydropyranyl or triphenylmethyl optionally substituted by halogen or by lower alkoxy, such as methoxy, or optionally substituted alkylidene radicals that bond the oxygen atoms in the 4-and 6-position of the glucose moiety. Such alkylidene radicals are especially a lower alkylidene radical, more especially the ethylidene, isopropylidene or propylidene radical, or alternatively an optionally substituted benzylidene radical, preferably substituted in the p-position.

These protecting groups can be split off in a manner known per se. It is thus possible to remove them by acid hydrolysis, in the case of benzyl or benzylidene radicals also by hydrogenolysis, for example with hydrogen in the presence of a noble metal catalyst, such as a palladium or platinum catalyst.

The following Examples serve to illustrate the invention. Temperatures are given in degrees Centigrade.

EXAMPLE 1

Manufacture of 1000 capsules each containing 260 mg of active ingredients:

| Composition | |
|---|---|
| rifampicin | 250 g |
| N—acetylmuramyl-L-alanyl-D-isoglutaminyl-L-alanyl-2-(1',2'-dipalmitoyl-sn-glycero-3'-hydroxyphosphoryloxy)-ethylamide in admixture with from 40 to 55% of the sodium salt | 10 g |
| talc | 36 g |
| wheat starch | 24 g |
| magnesium stearate | 16 g |
| lactose | 4 g |
| | 340 g |

Preparation

The pulverulent substances are forced through a sieve having a mesh width of 0.6 mm and mixed thoroughly. Gelatin capsules are each filled with 340 mg of this mixture using a capsule filling machine.

EXAMPLE 2

Manufacture of 1000 capsules each containing 105 mg of active substances:

| Composition | |
|---|---|
| rifampicin | 100 g |
| N—acetyldesmethylmuramyl-L-alanyl-D-isoglutaminyl-2-(1,2'-dipalmitoyl-sn-glycero-3'-hydroxyphosphoryloxy)-ethylamide in admixture with from 40 to 55% of the sodium salt | 5 g |
| ethylcellulose | 3 g |
| stearatic acid | 3 g |
| | 111 g |

Preparation

The ethylcellulose and the stearic acid are dissolved in 120 ml of methylene chloride, the antibiotic is added and the composition is forced through a sieve of 0.6 mm mesh width at a temperature of approximately 40° C., the methylene chloride evaporating off. Gelatin capsules having a capacity of 0.5 ml are filled with 156 mg of the resulting granulate using a capsule filling machine.

EXAMPLE 3

Manufacture of an animal feedstuff containing 0.005% of active substances.

| Premix | |
|---|---|
| rifampicin or chlorotetracycline | 30 g |
| N—benzoyldesmethylmuramyl-L-alanyl-D-isoglutaminyl-2-(1',2'-dipalmitoyl-sn-glycero-3'-hydroxyphosphoryloxy)-ethylamide in admixture with from 40 to 55% of the sodium salt | 10 g |
| sugar powder | 50 g |
| soybean feed (extracted with solvents) | 275 g |
| | 365 g |
| Additives | |
| corn meal | 500.0 kg |
| soybean flour, 44% protein | 300.0 kg |
| alfalfa flour | 13.5 kg |
| dicalcium phosphate | 18.0 kg |
| calcium carbonate (ground) | 4.5 kg |
| salt | 2.3 kg |
| fish meal, 60% protein | 18.0 kg |
| stabilisted fat | 27.0 kg |
| dry whey residue | 18.0 kg |
| manganese sulfate | 0.2 kg |
| zinc oxide | 1.3 kg |
| d,l-methionine | 0.7 kg |

| vitamin premix | 4.5 kg |
|---|---|
| | 908.0 kg |

The vitamin premix contains in 4.5 kg: 16,000,000 I.U. of vit. A, 1,000,000 I.U. of vit. D$_3$, 5,000 I.U. of vit. E acetate, 6 g of vit. K$_3$, 6 mg of vit. B$_{12}$, 3 g of riboflavin, 30 g of niacin, 5 g of calcium pantothenate and 100 g of ethoxyquin (1,2-dihydro-6-ethoxy-2,2,4-trimethylquinoline) and corn meal to make up 4.5 kg.

Method of Preparation

The active substances and sugar are thoroughly mixed, the mixture is forced through a sieve of 0.6 mm mesh width and then mixed with the soybean flour. The premix is then added to the animal feedstuff in an amount corresponding to the desired final concentration and the whole is then homogenised in a horizontal drum mixer.

EXAMPLE 4

Laboratory white mice are infected i.p. with $2 \times 10^4$ cfu (colony forming units) of *Klebsiella pneumoniae*, $0.1 \times 10^4$ cfu of *Pasteurella multocida* or $40 \times 10^4$ cfu of *Salmonella typhimurium* in salt solution so that 90 to 100% of the untreated control animals die within 48 hours. Immediately after infection and 3 hours after infection, groups of 10 mice are treated with cefroxadin, both alone (without muramylpeptide) and in combination with 10 mg/kg of N-acetylmuramyl-L-alanyl-D-isoglutaminyl-L-alanyl-2-(1',2'-dipalmitoyl-sn-glycero-3'-hydroxyphosphoryloxy)-ethylamide, these being administered twice subcutaneously in the form of aqueous solutions or suspensions. A count of the surviving animals was made 4 and 10 days after infection. The ED$_{50}$ values [mg/kg] for the antibiotic were lower by a multiple when administered in combination with the muramylpeptide.

EXAMPLE 5

In a manner analogous to that described in Examples 1 and 2 combination preparations are obtained which in addition to the adjuncts and carriers contain the following active ingredients (from 40 to 55% of muramylpeptides in the form of sodium salts) in the specified amounts per capsule:

(a) 500 mg of cephalexin and 5 mg of N-acetylmuramyl-L-alanyl-D-isoglutaminyl-2-(1',2'-dihexadecyl-rac-glycero-3'-hydroxyphosphoryloxy)-ethylamide, (b) 750 mg of ampicillin and 40 mg of N-benzoylnormuramyl(α-methylalanyl)-D-isoglutaminyl-2-(1',2'-dioleoyl-sn-glycero-2'-hydroxyphosphoryloxy)-ethylamide, (c) 100 mg of doxycycline and 15 mg of N-acetylmuramyl-L-alanyl-D-glutamyl-2-(1'-hexadecyl-rac-glycero-3'-hydroxyphosphoryloxy)-ethylamide, (d) 300 mg of methacryline and 15 mg of N-benzoyl-desmethylmuramyl-L-alanyl-D-glutamyl-γ-methyl ester-α-2-(1',2'-distearoyl-sn-glycero-3'-hydroxyphosphoryloxy)-ethylamide, (e) 250 mg of erythromycin estolate and 30 mg of N-propionyldesmethylmuramyl-L-α-aminobutyryl-D-isoglutaminyl-γ-oxymethylcarbonyl-2-(1',3'-di[(3"R)-hydroxy-(2"S)palmitoylaminooctadecyloxy)-2'-hydroxyphosphoryloxy]-ethylamide.

EXAMPLE 6

Manufacture of a sterile dry substance for injection (lyophilisation)

500 mg of cefsulodin and 10 mg of N-acetylmuramyl-N-methyl-L-alanyl-N,N'-dimethylglutaminyl-2-(1',2'-dipalmitoyl-sn-glycero-3'-hydroxyphosphoryloxy)-ethylamide in admixture with from 40 to 55% of the sodium salt are dissolved, while stirring, in 5 ml of water. The solution is sterile-filtered and, under aseptic conditions, is introduced into a sterile ampoule (phial) and lyophilised. The dry substance can be used for parenteral administration after dissolving in water or physiological solutions.

EXAMPLE 7

Manufacture of a sterile dry substance for injection (powder filling)

500 mg of sterile cefsulodin and 15 mg of sterile N-acetyldesmethylmuramyl-L-alanyl-D-isoglutaminyl-2-(1'-palmitoyl-2'-oleoyl-sn-glycero-3'-hydroxyphosphoryloxy)-ethylamide (in admixture with from 40 to 55% of the sodium salt) are, under aseptic conditions, homogeneously mixed and introduced into an ampoule. The dry substance can be used for parental administration after dissolving in water or physiological solutions.

EXAMPLE 8

In a manner analogous to that described in Examples 6 and 7 sterile dry substance mixtures for injection are obtained that contain the following amounts of effective constituents (muramylpeptides in admixture with from 40 to 55% of their sodium salt):

(a) 1000 mg of oxacillin (sodium salt) and 20 mg of N-acetylmuramyl-L-alanyl-D-isoglutaminyl-L-alanyl-2-(3'-palmitoyl-rac-glycero-1'-hydroxyphosphoryloxy)-ethylamide, (b) 500 mg of cefazolin and 10 mg of N-acetyldesmethylmuramyl-L-prolyl-D-glutaminylglycyl-2-(1',2'-dimyristoyl-sn-glycero-3'-hydroxyphosphoryloxy)-ethylamide, (c) 80 mg of gentamycin and 1 mg of N-4-(methylbenzoyl)desmethylmuramyl-L-valyl-D-glutaminyl-2-(1',2'-dilauroyl-sn-glycero-3'-hydroxyphosphoryloxy)-ethylamide, (d) 200 mg of doxycycline and 0.2 mg of N-propionyldesmethylmuramyl-L-seryl-D-isoglutaminyl-2-(1',2'-dilinoloyl-sn-glycero-3'-hydroxyphosphoryloxy)-ethylamide, (e) 50 mg of amphotericin B, 41 mg of sodium desoxycholate and 0.05 mg of N-acetylmuramyl-L-lysyl-D-isoglutaminyl-2-(1',2'-distearoyl-sn-glycerohydroxyphosphoryloxy)-ethylamide for the manufacture of the stock solution, (f) 500 mg of vancomycin and 0.01 mg of N-4-methoxybenzoylnormuramyl-L-threonyl-D-isoglutaminyl-2-(1',2'-dioleoyl-sn-glycero-3'-hydroxyphosphoryloxy)-ethylamide.

The muramylpeptides of the formula I serving as the starting materials for the manufacture of the combination preparations according to the invention are manufactured, for example, in a manner analogous to that described in the following Examples.

The compounds of the formula I cannot be characterised by a melting point nor is spectroscopic data, such as NMR and IR spectra, suitable for accurate characterisation.

The data provided by $R_f$ values is also unsuitable for precise characterisation because of the dominant nature of the lipid constituents.

Since, however, the structure of the starting materials is known accurately (cf. German Offenlegungsschrift No. 26 55 500; the phospholipid constituent used in each case is commercially available) and since the linking of phospholipid and muramylpeptide is clear, the sequence of the units in the end product and the structure of the end product is thus also clearly determined.

EXAMPLE 9

A solution of 2 mmol of N-acetylmuramyl-L-alanyl-D-isoglutamine-N-hydroxysuccinimide ester in 6.5 ml of dimethylacetamide is added dropwise to a solution of 1.4 mmol of 2-(1,2-dipalmitoyl-sn-glycero-3-hydroxyphosphoryloxy)-ethylamine and 2.5 mmol of triethylamine in 25 ml of a mixture of chloroform, methanol and water in the ratio 65:25:4. After stirring for 18 hours at 20° C., the solution is concentrated under reduced pressure to approximately 15 ml producing an emulsion. This emulsion is diluted with 200 ml of water and freeze-dried. The residue is suspended in 30 ml of water and dialyzed first of all against water, then against a 0.1 molar solution of sodium phosphate buffer pH 7 and subsequently extensively against water. The internal dialysate, which contains the desired product and residues of dicyclohexylurea, is diluted with water to make up 150 ml and is centrifuged for one hour at 30,000 g. The supernatant liquid, which contains a mixture of pure N-acetylmuramyl-L-alanyl-D-isoglutaminyl-2-(1',2'-dipalmitoyl-sn-glycero-3'-hydroxyphosphoryloxy)-ethylamide with from 40 to 55 mole % of its sodium salt, is freeze-dried. In a thin-layer chromatogram on silica gel the compound exhibits the following $R_f$ values: 0.31 (in chloroform/methanol/water, 65:25:4) and 0.64 (in chloroform/methanol/acetic acid/water, 25:15:4:2).

The novel compound is characterized analytically in that the units N-acetylmuraminic acid, palmitic acid, phosphate, L-alanine and D-glutaminic acid are determined quantitatively: N-acetylmuraminic acid is determined spectrophotometrically with the aid of the Morgan Elson reaction according to the modification of J. M. Ghuysen et al [in "Methods in Enzymology" 8, 629 (1966)].

Phosphate is determined quantitatively according to Lowry et al [J. Biol. Chem. 207, 1 (1954)].

Palmitic acid and the amino acids are determined by gas chromatography in a total hydrolysate (6 N HCl, 24 hours, 110° C.) or quantitatively with the aid of an amino acid analyser using pentadecanoic acid or norleucine as internal standards.

The molar ratios found, calculated on phosphate, are as follows:

$PO_4'''$: N-acetylmuraminic acid:L-alanine:D-glutaminic acid:palmitic acid = 1:0.92:0.91:0.95:2.18.

The N-acetylmuramyl-L-alanyl-D-isoglutamine-N-hydroxysuccinimide ester, which is used as starting material, may be prepared, for example, as follows:

2 mmol of N-acetylmuramyl-L-alanyl-D-isoglutamine, 2.2 mmol of N-hydroxysuccinimide and 2.2 mmol of dicyclohexylcarbodiimide are dissolved in 6.5 ml of dimethylacetamide and stirred for 18 hours at 20° C. The precipitated dicyclohexylurea is separated off and the solution is used directly for the condensation with the phospholipid.

The 2-(1,2-dipalmitoyl-sn-glycero-3-hydroxyphosphoryloxy)-ethyl amine, which is used as starting material, is a commercially available synthetic preparation.

EXAMPLE 10

N-acetylmuramyl-L-alanyl-D-isoglutaminyl-L-alanyl-2-(1',2'-dipalmitoyl-sn-glycero-3'-hydroxyphosphoryloxy)-ethylamide is obtained in a manner analogous to that of Example 9 using 2-(1,2-dipalmitoyl-sn-glycero-3-hydroxyphosphoryloxy)-ethylamine and N-acetylmuramyl-L-alanyl-D-isoglutaminyl-L-alanine-N-hydroxysuccinimide ester as starting materials. $R_f$ value in a thin-layer chromatogram on silica gel: 0.3 (in the system chloroform/methanol/water, 65:25:4).

We claim:

1. Pharmaceutical preparations with antibiotic activity comprising an antibiotically effective amount of a combination of at least one antibiotic and an amount effective to increase the activity of said antibiotic of at least one muramylpeptide of the formula (I)

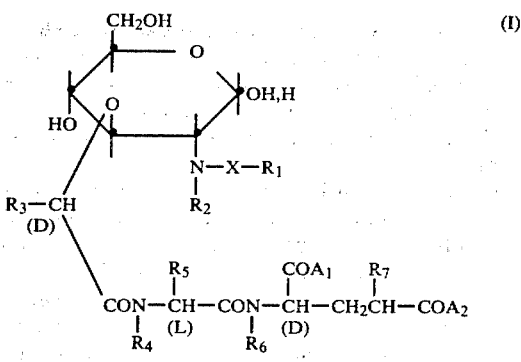

wherein

X represents carbonyl or carbonyloxy, $R_1$ represents optionally substituted alkyl or aryl, $R_2$, $R_4$ and $R_6$ represent hydrogen or lower alkyl, $R_3$ represents hydrogen or lower alkyl, $R_5$ represents hydrogen, lower alkyl, free or functionally modified hydroxy-lower alkyl, free or functionally modified mercapto-lower alkyl, optionally substituted amino-lower alkyl, cycloalkyl, cycloalkyl-lower alkyl, optionally substituted aryl or aralkyl, nitrogen-containing heterocyclyl or heterocyclyl-lower alkyl, or $R_4$ and $R_5$ together represent also alkylene having 3 or 4 carbon atoms, $R_7$ represents hydrogen or optionally esterified or amidated carboxyl, and one of the radicals $A_1$ and $A_2$ represents a radical of the formula

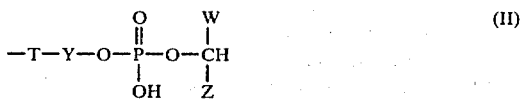

wherein

T represents NH or O,

Y represents an optionally substituted alkylene group that can also be interrupted by one or two oxycarbonyl and/or iminocarbonyl groups, W represents hydrogen, and Z represents a 1,2-dihydroxyethyl or 2-hydroxyethyl group in which at least one hydroxy group is esterified by an optionally unsaturated long-chain aliphatic carboxylic acid or etherified by an optionally unsaturated long-chain aliphatic alcohol, or each of W and Z represents a hydroxymethyl group esterified by an optionally unsaturated long-chain aliphatic carboxylic acid or etherified by an optionally unsaturated long-chain aliphatic alcohol, and the other of the radicals $A_1$ and $A_2$ represents free or etherified hydroxy, free or alkylated amino, lower alkylamino or aminocarbonyl-lower alkylamino, and/or a pharmaceutically acceptable salt thereof together with a significant amount of a pharmaceutically acceptable carrier.

2. Preparations according to claim 1 that contain at least one antibiotic from the group consisting of β-lactam antibiotics, aminoglycosides, tetracyclines, macrolides, lincomycins, polyene antibiotics, polypeptide antibiotics, anthracyclines, chloramphenicols and thiamphenicols, cycloserines, fusidic acids or rifamycins.

3. Preparations according to claim 1 that contain as antibiotic a penicillin, cephalosporin, penem, nocardicin, thienamycin, a clavulanic compound, a streptomycin, neomycin, tobramycins, a kanamycin, gentamycin or sisomycin.

4. Preparations according to claim 1 that contain as antibiotic amoxycillin, ampicillin, carbenicillin, cloxacillin, cyclacillin, dicloxacillin, mecillinam, methicillin, penicillin G, penicillin V, pivampicillin, sulbenicillin, azlocillin, ticarcillin, mezlocillin, pivmecillinam, 6-(4-endoazatricyclo[5.2.2.0$^{2,6}$]undec-8-enyl)-methyleneaminopenicillanic acid, cefaclor, cefazaflur, cefazolin, cefadroxil, cefoxitin, cefuroxime, cephacetril, cephalexin, cephaloglycin, cephaloridines, cephalothin, cefamandole, cephanon, cephapirin, cefatrizine, cephradine, cefroxadin {(7β-[D-2-amino-2-(1,4-cyclohexadienyl)-acetamido]-3-methoxy-3-cephem-4-carboxylic acid}, cefsulodin, cefotaxime, cefotiam, ceftezole, cefazedon, nocardicin A, thienamycin, clavulanic acid, streptomycin, streptomycin A, neomycin B, tobramycin, dibekacin, mixtures of kanamycin A, B and C, amicacins, mixtures of gentamycin A, $C_1$, $C_2$ or $C_{1a}$, sisomycin, netilmycin, lividomycin, ribocamycin, paromomycin, tetracycline, doxycycline, chlorotetracycline, oxytetracycline, methacycline, maridomycin, spiramycins, erythromycins, oleandomycins, lincomycins, amphothericin B and the methyl ester thereof, nystalin, colistin, gramicidin S, polymyxin B, virginiamycin, tyrothricin, viomycin, vancomycin, rifamycin S, -SV, B or semisynthetic derivatives thereof.

5. Preparations according to claim 1 that contain as antibiotic cephacetril, cefadroxil, rifampicin, cefsulodin, cefroxadin, bicozamycin or cefotiam.

6. Preparations according to one of claims 1 to 5 that contain per dosage unit between 50 and 1000 mg of antibiotic and, in the case of orally administrable preparations, between 1 mg and 50 mg of muramylpeptide or, in the case of orally administrable coated tablets that are resistant to gastric juice or in the case of injectable preparations, between 0.01 mg and 50 mg of muramylpeptide, together with a pharmaceutically acceptable carrier.

7. Preparations according to one of claims 1 to 5 wherein X represents carbonyl, $R_1$ represents optionally substituted alkyl having up to 18 carbon atoms or aryl having up to 30 carbon atoms, $R_2$, $R_3$, $R_4$ and $R_6$ represent hydrogen or lower alkyl, $R_5$ represents hydrogen; lower alkyl optionally substituted by hydroxy, lower alkoxy, mercapto, lower alkylmercapto, amino, lower alkylamino or by halogen; cycloalkyl or cycloalkyl-lower alkyl, wherein the cyloalkyl radical contains from 4 to 6 carbon atoms; optionally substituted phenyl or phenyl-lower alkyl; heterocycyl or heterocyclyl-lower alkyl, each having 5 or 6 ring members and containing one or two aza atoms, or $R_4$ and $R_5$ together represent also alkylene having 3 or 4 carbon atoms, $R_7$ represents hydrogen, and one of the radicals $A_1$ and $A_2$ represents a radical of the formula

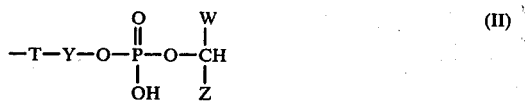

wherein T represents NH or O, Y represents optionally substituted alkylene that has up to 20 carbon atoms and can also be interrupted by carbonyloxy or carbonylimino, W represents hydrogen, and Z represents a 1,2-dihydroxyethyl or 2-hydroxyethyl group in which at least one hydroxy group is esterified by an optionally unsaturated long-chain aliphatic carboxylic acid having up to 30 carbon atoms or by a mycolic acid, or is etherified by an optionally unsaturated long-chain aliphatic alcohol having up to 30 carbon atoms, or each of W and Z represents a hydroxymethyl group esterified by an optionally unsaturated long-chain aliphatic carboxylic acid having up to 30 carbon atoms or by a mycolic acid or etherified by an optionally unsaturated long-chain aliphatic alcohol having up to 30 carbon atoms, and the other of the radicals $A_1$ and $A_2$ represents free or etherified hydroxy, amino, lower alkylamino or aminocarbonyl-lower alkylamino.

8. Preparations according to one of claims 1 to 5 wherein X represents carbonyl, $R_1$ represents lower alkyl optionally substituted by hydroxy, lower alkoxy or by halogen; or phenyl optionally substituted by hydroxy, lower alkoxy, lower alkyl or by halogen, $R_2$, $R_4$ and $R_6$ represent hydrogen or methyl, $R_3$ represents hydrogen, methyl or ethyl, $R_5$ represents hydrogen; lower alkyl having from 1 to 7 carbon atoms optionally substituted by hydroxy, lower alkoxy, mercapto, lower alkylmercapto or by halogen; 4-aminobutyl; cycloalkyl or cycloalkyl-lower alkyl wherein the cycloalkyl radical contains from 4 to 6 carbon atoms and the lower alkyl radical contains from 1 to 3 carbon atoms; phenyl or phenyl-lower alkyl having from 1 to 3 carbon atoms in the lower alkyl radical and optionally substituted by hydroxy, lower alkoxy or by halogen; 4-imidazolylmethyl or 3-indolylmethyl, or $R_4$ and $R_5$ together represent also alkylene having 3 or 4 carbon atoms, $R_7$ represents hydrogen and one of the radicals $A_1$ and $A_2$ represents a radical of the formula

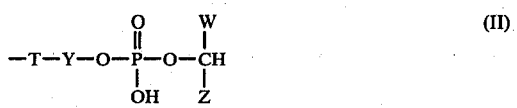

wherein T represents NH or O, Y represents lower alkylene or a radical of the formulae

or

—Y₁—CONH—Y₂ (IIIe)

in which each of $Y_1$ and $Y_2$ independently of the other represents lower alkylene that has from 1 to 7 carbon atoms and is optionally substituted by lower alkyl, W represents hydrogen and Z represents a 1,2-dihydroxyethyl or 2-hydroxyethyl group in which at least one hydroxy group is esterified by an aliphatic carboxylic acid having from 14 to 24 carbon atoms and optionally containing one or two unsaturated bonds, or by a natural or synthetic mycolic acid or etherified by an aliphatic alcohol having from 10 to 20 carbon atoms and optionally containing one to two unsaturated bonds, or each of W and Z represents a hydroxymethyl group esterified by an aliphatic carboxylic acid having from 16 to 22 carbon atoms and optionally containing one or two unsaturated bonds, or by a natural or synthetic mycolic acid or etherified by an aliphatic alcohol having from 12 to 18 carbon atoms and optionally containing one or two unsaturated bonds, and the other of the radicals $A_1$ and $A_2$ is hydroxy, lower alkoxy, amino, lower alkylamino or aminocarbonyl-lower alkylamino.

9. Preparations according to one of claims 1 to 5 wherein X represents carbonyl, $R_1$ represents lower alkyl or phenyl, $R_2$, $R_6$ and $R_7$ represent hydrogen, $R_3$ and $R_4$ represent hydrogen or methyl, $R_5$ represents hydrogen, lower alkyl having from 1 to 7 carbon atoms optionally substituted by phenyl, or $R_4$ and $R_5$ together represent also trimethylene, wherein $A_1$ represents hydroxy, lower alkoxy, amino, lower alkylamino or aminocarbonyl-lower alkylamino and $A_2$ represents a radical of the formula

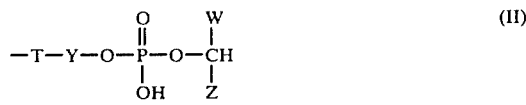

wherein T represents NH or O, Y represents ethylene or a radical of the formulae Y₁—COO—Y₂ or Y₁—CONH—Y₂

(IIIa)  (IIIe)

wherein each of $Y_1$ and $Y_2$ independently of the other represents unsubstituted lower alkylene, W is hydrogen and Z is a 1,2-dihydroxyethyl or 2-hydroxyethyl group in which at least one hydroxy group is esterified by an alkanecarboxylic acid having from 16 to 20 carbon atoms and optionally containing one or two unsaturated bonds, or etherified by an alkanol having from 12 to 18 carbon atoms and optionally containing one or two unsaturated bonds, or each of W and Z represents a hydroxymethyl group esterified by an alkanecarboxylic acid having from 16 to 22 carbon atoms and optionally containing one or two unsaturated bonds, or etherified by an alkanol having from 12 to 18 carbon atoms and optionally containing one or two unsaturated bonds, and those compounds in which the meanings for $A_1$ and $A_2$ are interchanged.

10. Preparations according to one of claims 1 to 5 wherein X represents carbonyl, $R_1$ represents lower alkyl or phenyl, $R_2$, $R_4$, $R_6$ and $R_7$ represent hydrogen, $R_3$ represents hydrogen or methyl, $R_5$ represents lower alkyl having from 1 to 3 carbon atoms, $A_1$ represents amino and $A_2$ represents a radical of the formula

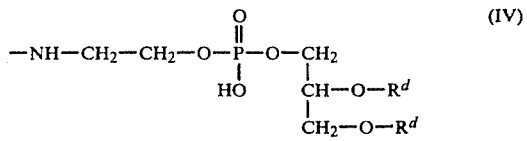

wherein $R^d$ represents the acyl radical of an alkanecarboxylic acid having from 16 to 20 carbon atoms and optionally containing one or two unsaturated bonds.

11. Method for increasing the activity of antibiotics in mammals including man comprising administering to said mammals at least one antibiotic and an amount effective to increase the activity of said antibiotic of at least one muramylpeptide according to claim 1.

12. Animal feedstuffs and feedstuff additives that contain an antibiotically effective amount of a combination comprising at least one antibiotic and an amount effective to increase the activity of said antibiotic of at least one muramylpeptide according to claim 1.

13. A pharmaceutical preparation according to claim 1, that contains an effective amount of amphotericin B and the sodium salt of N-acetyl-muramyl-L-alanyl-D-isoglutaminyl-L-alanyl-2-(1',2'-dipalmitoyl-sn-glycero-3'-hydroxyphosphoryloxy)ethylamide, together with a pharmaceutically acceptable carrier.

14. Preparations according to claim 7 that contain per dosage unit between 50 and 1000 mg of antibiotic and, in the case of orally administrable preparations, between 1 mg and 50 mg of muramylpeptide or, in the case of orally administrable coated tablets that are resistant to gastric juice or in the case of injectable preparations, between 0.01 mg and 50 mg of muramylpeptide, together with a pharmaceutically acceptable carrier.

15. Preparations according to one of claims 1 to 5 wherein X represents carbonyl, $R_1$ represents lower alkyl optionally substituted by hydroxy, lower alkoxy or by halogen; or phenyl optionally substituted by hydroxy, lower alkoxy, lower alkyl or by halogen, $R_2$, $R_4$ and $R_6$ represent hydrogen or methyl, $R_3$ represents hydrogen, methyl or ethyl, $R_5$ represents hydrogen; lower alkyl having from 1 to 7 carbon atoms optionally substituted by hydroxy, lower alkoxy, mercapto, lower alkylmercapto or by halogen; 4-aminobutyl; cycloalkyl or cycloalkyl-lower alkyl wherein the cycloalkyl radical contains from 4 to 6 carbon atoms and the lower alkyl radical contains from 1 to 3 carbon atoms; phenyl or phenyl-lower alkyl having from 1 to 3 carbon atoms in the lower alkyl radical and optionally substituted by hydroxy, lower alkoxy or by halogen; 4-imidazolylmethyl or 3-indolylmethyl, or $R_4$ and $R_5$ together represent also alkylene having 3 or 4 carbon atoms, $R_7$ represents hydrogen and one of the radicals $A_1$ and $A_2$ represents a radical of the formula

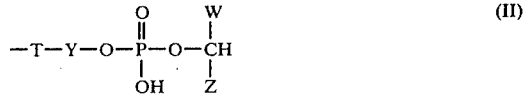

wherein T represents NH or O, Y represents lower alkylene or a radical of the formulae —Y₁—COO—Y₂ (IIIa)

or $$-Y_1-CONH-Y_2 \quad \text{(IIIe)}$$

in which each of $Y_1$ and $Y_2$ independently of the other represents lower alkylene that has from 1 to 7 carbon atoms and is optionally substituted by lower alkyl, W represents hydrogen and Z represents a 1,2-dihydroxyethyl or 2-hydroxyethyl group in which at least one hydroxy group is esterified by an aliphatic carboxylic acid having from 14 to 24 carbon atoms and optionally containing one or two unsaturated bonds, or by a natural or synthetic mycolic acid or etherified by an aliphatic alcohol having from 10 to 20 carbon atoms and optionally containing one or two unsaturated bonds, or each of W and Z represents a hydroxymethyl group esterified by an aliphatic carboxylic acid having from 16 to 22 carbon atoms and optionally containing one or two unsaturated bonds, or by a natural or synthetic mycolic acid or etherified by an aliphatic alcohol having from 12 to 18 carbon atoms and optionally containing one of two saturated bonds, and the other of the radicals $A_1$ and $A_2$ is hydroxy, lower alkoxy, amino, lower alkylamino or aminocarbonyl-lower alkylamino.

16. Preparations according to one of claims 1 to 5 wherein X represents carbonyl, $R_1$ represents lower alkyl or phenyl, $R_2$, $R_6$ and $R_7$ represent hydrogen, $R_3$ and $R_4$ represent hydrogen or methyl, $R_5$ represents hydrogen, lower alkyl having from 1 to 7 carbon atoms optionally substituted by phenyl, or $R_4$ and $R_5$ together represent also trimethylene, wherein $A_1$ represents hydroxy, lower alkoxy, amino, lower alkylamino or aminocarbonyl-lower alkylamino and $A_2$ represents a radical of the formula

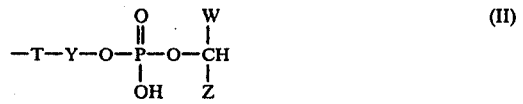

wherein T represents NH or O, Y represents ethylene or a radical of the formulae $$Y_1-COO-Y_2 \text{ or } Y_1-CONH-Y_2$$

(IIIa)     (IIIe)

wherein each of $Y_1$ and $Y_2$ independently of the other represents lower alkylene which is unsubstituted or substituted by lower alkyl, W is hydrogen and Z is a 1,2-dihydroxyethyl or 2-hydroxyethyl group in which at least one hydroxy group is esterified by an alkanecarboxylic acid having from 16 to 20 carbon atoms and optionally containing one or two unsaturated bonds, or etherified by an alkanol having from 12 to 18 carbon atoms and optionally containing one or two unsaturated bonds, or each of W and Z represents a hydroxymethyl group esterified by an alkanecarboxylic acid having from 16 to 22 carbon atoms and optionally containing one or two unsaturated bonds, or etherified by an alkanol having from 12 to 18 carbon atoms and optionally containing one or two unsaturated bonds, and those compounds in which the meanings for $A_1$ and $A_2$ are interchanged.

17. Preparations according to one of claims 1 to 5 that contain N-acetyl-muramyl-L-alanyl-D-isoglutaminyl-L-alanine-2-(1',2'-dipalmitoyl-sn-glycero-3'-hydroxy-phosphoryloxy)-ethylamide-sodium-salt.

18. Method according to claim 11, characterised in that the antibiotic is selected from the group consisting of β-lactam antibiotics, aminoglycosides, tetracyclines, macrolides, lincomycins, polyene antibiotics, polypeptide antibiotics, antracyclines, chloramphenicols and thiamphenicols, cycloserines, fusidic acids or rifamycins.

19. Method according to claim 11, characterised in that the antibiotic is a penicillin, cephalosporin, penem, nocardicin, thienamycin, a clavulanic compound, a streptomycin, neomycin, tobramycin, a kanamycin, gentamycin or sisomycin.

20. Method according to claim 11, characterised in that the antibiotic is amoxycillin, ampicillin, carbenicillin, cloxacillin, cyclacillin, dicloxacillin, mecillinam, methicillin, penicillin G, penicillin V, pivampicillin, sulbenicillin, azlocillin, ticarcillin, mezlocillin, pivmecillinam, 6-(4-endoazatricyclo[5,2,0$^{2,6}$]undec-8-enyl)-methyleneaminopenicillanic acid, cefaclor, cefazaflur, cefazolin, cefadroxil, cefoxitin, cefuroxime, cephacetril, cephalexin, cephaloglycin, cephaloridine, cephalothin, cefamandole, cephanon, cephapirin, cefatrizine, cephradine, cefroxadin {(7β-[D-2-amino-2-(1,4-cyclohexadienyl)-acetamido]-3-methoxy-3-cephem-4-carboxylic acid}, cefsulodin, cefotaxime, cefotiam, ceftezole, cefazedon, nocardicin A, thienamycin, clavulanic acid, streptomycin, streptomycin A, neomycin B, tobramycin, dibekacin, mixtures of kanamycin A, B and C, an amicacin, a mixture of gentamycin A, $C_1$, $C_2$ or $C_{1a}$, sisomycin, netilmycin, lividomycin, ribocamycin, paromomycin, tetracycline, doxycycline, chlorotetracycline, oxytetracycline, methacycline, maridomycin, spiramycin, an erythromycin, oleandomycin, a lincomycin, amphothericin B and the methyl ester thereof, nystalin, colistin, gramicidin S, polymyxin B, virginiamycin, tyrothricin, viomycin, vancomycin, rifamycin S, -SV, B or a semisynthetic derivative thereof.

21. Method according to claim 11, characterised in that the antibiotic is cephacetril, cefadroxil, rifampicin, cefsulodin, cefroxadin, bicozamycin or cefotiam.

22. Method according to one of claims 11 and 18 to 21, characterised in that in the muramylpeptide X represents carbonyl, $R_1$ represents optionally substituted alkyl having up to 18 carbon atoms or aryl having up to 30 carbon atoms, $R_2$, $R_3$, $R_4$ and $R_6$ represent hydrogen or lower alkyl, $R_5$ represents hydrogen; lower alkyl optionally substituted by hydroxy, lower alkoxy, mercapto, lower alkylmercapto, amino, lower alkylamino or by halogen; cycloalkyl or cycloalkyl-lower alkyl, wherein the cycloalkyl radical contains from 4 to 6 carbon atoms; optionally substituted phenyl or phenyl-lower alkyl; heterocycyl or heterocyclyl-lower alkyl, each having 5 or 6 ring members and containing one or two aza atoms, or $R_4$ and $R_5$ together represent also alkylene having 3 or 4 carbon atoms, $R_7$ represents hydrogen, and one of the radicals $A_1$ and $A_2$ represents a radical of the formula

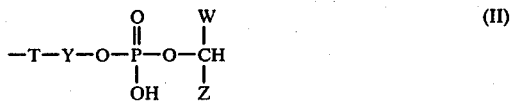

wherein T represents NH or O, Y represents optionally substituted alkylene that has up to 20 carbon atoms and can also be interrupted by carbonyloxy or carbonylimino, W represents hydrogen, and Z represents a 1,2-dihydroxyethyl or 2-hydroxyethyl group in which at least one hydroxy group is esterfied by an optionally unsaturated long-chain aliphatic carboxylic acid having up to 30 carbon atoms or by a mycolic acid, or is etherified by an optionally unsaturated long-chain aliphatic alcohol having up to 30 carbon atoms, or each of W and Z represents a hydroxymethyl group esterified by an optionally unsaturated long-chain aliphatic carboxylic acid having up to 30 carbon atoms or by a mycolic acid or etherified by an optionally unsaturated long-chain aliphatic alcohol having up to 30 carbon atoms, and the other of the radicals $A_1$ and $A_2$ represents free or etherified hydroxy, amino, lower alkylamino or aminocarbonyl-lower alkylamino.

23. Method according to one of claims 11 and 18 to 21, characterised in that in the muramylpeptide X represents carbonyl, $R_1$ represents lower alkyl optionally substituted by hydroxy, lower alkoxy or by halogen; or phenyl optionally substituted by hydroxy, lower alkoxy, lower alkyl or by halogen, $R_2$, $R_4$ and $R_6$ represent hydrogen or methyl, $R_3$ represents hydrogen, methyl or ethyl, $R_5$ represents hydrogen; lower alkyl having from 1 to 7 carbon atoms optionally substituted by hydroxy, lower alkoxy, mercapto, lower alkylmercapto or by halogen; 4-aminobutyl; cycloalkyl or cycloalkyl-lower alkyl wherein the cycloalkyl radical contains from 4 to 6 carbon atoms and the lower alkyl radical contains from 1 to 3 carbon atoms; phenyl or phenyl-lower alkyl having from 1 to 3 carbon atoms in the lower alkyl radical and optionally substituted by hydroxy, lower alkoxy or by halogen; 4-imidazolylmethyl or 3-indolylmethyl, or $R_4$ and $R_5$ together represent also alkylene having 3 or 4 carbon atoms, $R_7$ represents hydrogen and one of the radicals $A_1$ and $A_2$ represents a radical of the formula

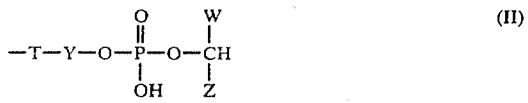

wherein T represents NH or O, Y represents lower alkylene or a radical of the formulae

or

in which each of $Y_1$ and $Y_2$ independently of the other represents lower alkylene that has from 1 to 7 carbon atoms and is optionally substituted by, lower alkyl, W represents hydrogen and Z represents a 1,2-dihydroxyethyl or 2-hydroxyethyl group in which at least one hydroxy group is esterified by an aliphatic carboxylic acid having from 14 to 24 carbon atoms and optionally containing one or two unsaturated bonds, or by a natural or synthetic mycolic acid or etherified by an aliphatic alcohol having from 10 to 20 carbon atoms and optionally containing one or two unsaturated bonds, or each of W and Z represents a hydroxymethyl group esterified by an aliphatic carboxylic acid having from 16 to 22 carbon atoms and optionally containing one or two unsaturated bonds, or by a natural or synthetic mycolic acid or etherified by an aliphatic alcohol having from 12 to 18 carbon atoms and optionally containing one or two unsaturated bonds, and the other of the radicals $A_1$ and $A_2$ is hydroxy, lower alkoxy, amino, lower alkylamino or aminocarbonyl-lower alkylamino.

24. Method according to one of claims 11 and 18 to 21, characterised in that in the muramylpeptide X represents carbonyl, $R_1$ represents lower alkyl or phenyl, $R_2$, $R_6$ and $R_7$ represent hydrogen, $R_3$ and $R_4$ represent hydrogen or methyl, $R_5$ represents hydrogen, lower alkyl having from 1 to 7 carbon atoms optionally substituted by phenyl, or $R_4$ and $R_5$ together represent also trimethylene, wherein $A_1$ represents hydroxy, lower alkoxy, amino, lower alkylamino or aminocarbonyl-lower alkylamino and $A_2$ represents a radical of the formula

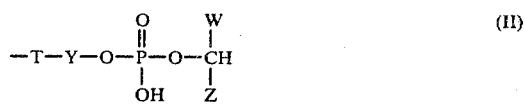

wherein T represents NH or O, Y represents ethylene or a radical of the formulae

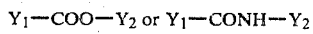

wherein each of $Y_1$ and $Y_2$ independently of the other represents unsubstituted lower alkylene, W is hydrogen and Z is a 1,2-dihydroxyethyl or 2-hydroxyethyl group in which at least one hydroxy group is esterified by an alkanecarboxylic acid having from 16 to 20 carbon atoms and optionally containing one or two unsaturated bonds, or etherified by an alkanol having from 12 to 18 carbon atoms and optionally containing one or two unsaturated bonds, or each of W and Z represents a hydroxymethyl group esterified by an alkanecarboxylic acid having from 16 to 22 carbon atoms and optionally containing one or two unsaturated bonds, or etherified by an alkanol having from 12 to 18 carbon atoms and optionally containing one or two unsaturated bonds, and those compounds in which the meanings for $A_1$ and $A_2$ are interchanged.

25. Method according to one of claims 11 and 18 to 21, characterised in that in the muramylpeptide X represents carbonyl, $R_1$ represents lower alkyl optionally substituted by hydroxy, lower alkoxy or by halogen; or phenyl optionally substituted by hydroxy, lower alkoxy, lower alkyl or by halogen, $R_2$, $R_4$ and $R_6$ represent hydrogen or methyl, $R_3$ represents hydrogen, methyl or ethyl, $R_5$ represents hydrogen; lower alkyl having from 1 to 7 carbon atoms optionally substituted by hydroxy, lower alkoxy, mercapto, lower alkylmercapto or by halogen; 4-aminobutyl; cycloalkyl or cycloalkyl-lower alkyl wherein the cycloalkyl radical contains from 4 to 6 carbon atoms and the lower alkyl radical contains from 1 to 3 carbon atoms; phenyl or phenyl-lower alkyl having from 1 to 3 carbon atoms in the lower alkyl radical and optionally substituted by hydroxy, lower alkoxy or by halogen; 4-imidazolylmethyl or 3-indolylmethyl, or $R_4$ and $R_5$ together represent also alkylene having 3 or 4 carbon atoms, $R_7$ represents hydrogen and one of the radicals $A_1$ and $A_2$ represents a radical of the formula

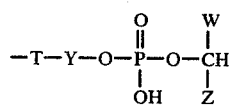 (II)

wherein T represents NH or O, Y represents lower alkylene or a radical of the formulae

 (IIIa)

or

 (IIIe)

in which each of $Y_1$ and $Y_2$ independently of the other represents lower alkylene that has from 1 to 7 carbon atoms and is optionally substituted by lower alkyl, W represents hydrogen and Z represents a 1,2-dihydroxyethyl or 2-hydroxyethyl group in which at least one hydroxy group is esterified by an aliphatic carboxylic acid having from 14 to 24 carbon atoms and optionally containing one or two unsaturated bonds, or by a natural or synthetic mycolic acid or etherified by an aliphatic alcohol having from 10 to 20 carbon atoms and optionally containing one or two unsaturated bonds, or each of W and Z represents a hydroxymethyl group esterified by an aliphatic carboxylic acid having from 16 to 22 carbon atoms and optionally containing one or two unsaturated bonds, or by a natural or synthetic mycolic acid or etherified by an aliphatic alcohol having from 12 to 18 carbon atoms and optionally containing one or two unsaturated bonds, and the other of the radicals $A_1$ and $A_2$ is hydroxy, lower alkoxy, amino, lower alkylamino or aminocarbonyl-lower alkylamino.

26. Method according to one of claims 11 and 18 to 21, characterised in that in the muramylpeptide X represents carbonyl, $R_1$ represents lower alkyl or phenyl, $R_2$, $R_6$ and $R_7$ represent hydrogen, $R_3$ and $R_4$ represent hydrogen or methyl, $R_5$ represents hydrogen, lower alkyl having from 1 to 7 carbon atoms optionally substituted by phenyl, or $R_4$ and $R_5$ together represent also trimethylene, wherein $A_1$ represents hydroxy, lower alkoxy, amino, lower alkylamino or aminocarbonyl-lower alkylamino and $A_2$ represents a radical of the formula

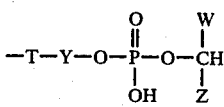 (II)

wherein T represents NH or O, Y represents ethylene or a radical of the formulae

(IIIa)     (IIIe)

wherein each of $Y_1$ and $Y_2$ independently of the other represents lower alkylene which is unsubstituted or substituted by lower alkyl, W is hydrogen and Z is a 1,2-dihydroxyethyl or 2-hydroxyethyl group in which at least one hydroxy group is esterified by an alkanecarboxylic acid having from 16 to 20 carbon atoms and optionally containing one or two unsaturated bonds, or etherified by an alkanol having from 12 to 18 carbon atoms and optionally containing one or two unsaturated bonds, or each of W and Z represents a hydroxymethyl group esterified by an alkanecarboxylic acid having from 16 to 22 carbon atoms and optionally containing one or two unsaturated bonds, or etherified by an alkanol having from 12 to 18 carbon atoms and optionally containing one or two unsaturated bonds, and those compounds in which the meanings for $A_1$ and $A_2$ are interchanged.

27. Method according to one of claims 11 and 18 to 21, characterised in that the muramylpeptide is N-acetyl-muramyl-L-alanyl-D-isoglutaminyl-L-al-anine-2-(1',2'-dipalmitoyl-sn-glycero-3'-hydroxyphosphoryloxy)-ethylamide-sodium-salt.

28. Preparations according to claim 16, that contain per dosage unit between 50 and 1000 mg of antibiotic and, in the case of orally administrable preparations, between 1 mg and 50 mg of muramylpeptide or, in the case of orally administrable coated tablets that are resistant to gastric juice or in the case of injectable preparations, between 0.01 mg and 50 mg of muramylpeptide, together with a pharmaceutically acceptable carrier.

29. Method according to claim 26, characterised in that between 50 and 1000 mg of antibiotic and 1 mg and 50 mg of muramylpeptide are used.

* * * * *